(12) United States Patent
Maeda et al.

(10) Patent No.: US 9,844,651 B2
(45) Date of Patent: Dec. 19, 2017

(54) BALLOON AND METHOD OF MANUFACTURING THE SAME

(71) Applicant: TERUMO KABUSHIKI KAISHA, Shibuya-ku, Tokyo (JP)

(72) Inventors: Naoyuki Maeda, Besancon (FR); Yoshiyuki Hashimoto, Hadano (JP); Kenichi Shimura, Machida (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 69 days.

(21) Appl. No.: 14/842,864

(22) Filed: Sep. 2, 2015

(65) Prior Publication Data
US 2015/0367109 A1    Dec. 24, 2015

Related U.S. Application Data

(63) Continuation of application No. PCT/JP2013/056793, filed on Mar. 12, 2013.

(51) Int. Cl.
*A61M 25/10* (2013.01)
*B29C 49/18* (2006.01)
(Continued)

(52) U.S. Cl.
CPC .... *A61M 25/1029* (2013.01); *A61M 25/1002* (2013.01); *B29C 49/18* (2013.01); *B29C 49/22* (2013.01); *B29C 49/6472* (2013.01); *B29C 49/78* (2013.01); *A61F 2/958* (2013.01); *A61M 2025/1075* (2013.01);
(Continued)

(58) Field of Classification Search
CPC ........... A61F 2/958; A61M 2025/1075; A61M 25/1029; B29C 49/22; B29C 49/80; B29L 2031/7543
See application file for complete search history.

(56) References Cited

U.S. PATENT DOCUMENTS

| 6,004,339 A | 12/1999 | Wijay |
| 6,946,092 B1 * | 9/2005 | Bertolino .......... A61M 25/1029 264/512 |
| 2012/0065718 A1 | 3/2012 | Simpson et al. |

FOREIGN PATENT DOCUMENTS

| JP | 2004-298354 A | 10/2004 |
| JP | 2012-066008 A | 4/2012 |

OTHER PUBLICATIONS

The extended European Search Report dated Nov. 4, 2016, by the European Patent Office in corresponding European Application No. 13878235.4. (8 pages).

(Continued)

*Primary Examiner* — Kevin C Sirmons
*Assistant Examiner* — Deanna K Hall
(74) *Attorney, Agent, or Firm* — Buchanan Ingersoll & Rooney PC

(57) ABSTRACT

A balloon in which a rupture in a circumferential direction can be prevented from occurring, and a method of manufacturing the same is disclosed. The balloon is configured to be arranged on a medical catheter, and includes a dilatable cylindrical portion formed with a birefringent polymer material. A ratio of the number of orientation distributions, calculated by dividing the number of orientation distributions of the cylindrical portion in a circumferential direction by the number of orientation distributions of the cylindrical portion in an axial direction, is less than 2.

9 Claims, 18 Drawing Sheets

(51) Int. Cl.
    *B29C 49/22* (2006.01)
    *B29C 49/64* (2006.01)
    *B29C 49/78* (2006.01)
    *A61F 2/958* (2013.01)
    *B29L 31/00* (2006.01)

(52) U.S. Cl.
    CPC ............... *A61M 2025/1088* (2013.01); *B29C 2949/78571* (2013.01); *B29C 2949/78806* (2013.01); *B29L 2031/7543* (2013.01)

(56) References Cited

OTHER PUBLICATIONS

Japanese Office Action (Notice of Reasons for Rejection) dated Jan. 26, 2016, by the Japanese Patent Office in corresponding Japanese Patent Application No. 2015-505123 (7 pgs).

International Search Report (PCT/ISA/210) dated May 28, 2013, by the Japanese Patent Office as the International Searching Authority for International Application No. PCT/JP2013/056793.

\* cited by examiner

FIG. 16

| | RUPTURE IN CIRCUMFERENTIAL DIRECTION | MEASUREMENT POINT | THE NUMBER OF ORIENTATION DISTRIBUTIONS | | | RATIO OF THE NUMBER OF ORIENTATION DISTRIBUTIONS (CIRCUMFERENTIAL DIRECTION/AXIAL DIRECTION) |
|---|---|---|---|---|---|---|
| | | | THICKNESS DIRECTION | AXIAL DIRECTION | CIRCUMFERENTIAL DIRECTION | |
| EXAMPLE 1 | NOT FOUND | CENTER ($P_2$) | 0.078 | 0.359 | 0.563 | 1.570 |
| | | DISTAL PORTION ($P_1$) | 0.097 | 0.352 | 0.551 | 1.565 |
| | | PROXIMAL PORTION ($P_3$) | 0.098 | 0.334 | 0.568 | 1.703 |
| EXAMPLE 2 | NOT FOUND | CENTER ($P_2$) | 0.169 | 0.319 | 0.512 | 1.602 |
| | | DISTAL PORTION ($P_1$) | 0.153 | 0.303 | 0.544 | 1.792 |
| | | PROXIMAL PORTION ($P_3$) | 0.149 | 0.299 | 0.552 | 1.849 |
| COMPARISON EXAMPLE 1 | FOUND | CENTER ($P_2$) | 0.077 | 0.330 | 0.593 | 1.797 |
| | | DISTAL PORTION ($P_1$) | 0.073 | 0.255 | 0.672 | 2.633 |
| | | PROXIMAL PORTION ($P_3$) | 0.074 | 0.340 | 0.587 | 1.726 |
| COMPARISON EXAMPLE 2 | FOUND | CENTER ($P_2$) | 0.078 | 0.298 | 0.624 | 2.091 |
| | | DISTAL PORTION ($P_1$) | 0.092 | 0.322 | 0.586 | 1.817 |
| | | PROXIMAL PORTION ($P_3$) | 0.069 | 0.355 | 0.576 | 1.625 |
| COMPARISON EXAMPLE 3 | FOUND | CENTER ($P_2$) | 0.076 | 0.303 | 0.621 | 2.053 |
| COMPARISON EXAMPLE 4 | FOUND | CENTER ($P_2$) | 0.124 | 0.250 | 0.627 | 2.510 |
| COMPARISON EXAMPLE 5 | FOUND | DISTAL PORTION ($P_1$) | 0.120 | 0.281 | 0.598 | 2.128 |
| | | PROXIMAL PORTION ($P_3$) | 0.117 | 0.262 | 0.621 | 2.376 |

FIG. 18

| | | INNER LAYER | INTERMEDIATE LAYER | | | OUTER LAYER |
|---|---|---|---|---|---|---|
| | | | INNER INTERFACE | CENTER | OUTER INTERFACE | |
| DISTAL PORTION (P₁) | THE NUMBER OF ORIENTATION DISTRIBUTIONS IN THICKNESS DIRECTION | 0.243 | 0.153 | 0.124 | 0.152 | 0.274 |
| | THE NUMBER OF ORIENTATION DISTRIBUTIONS IN AXIAL DIRECTION | 0.273 | 0.303 | 0.365 | 0.393 | 0.347 |
| | THE NUMBER OF ORIENTATION DISTRIBUTIONS IN CIRCUMFERENTIAL DIRECTION | 0.484 | 0.544 | 0.511 | 0.455 | 0.379 |
| CENTER (P₂) | THE NUMBER OF ORIENTATION DISTRIBUTIONS IN THICKNESS DIRECTION | 0.256 | 0.169 | 0.135 | 0.158 | 0.275 |
| | THE NUMBER OF ORIENTATION DISTRIBUTIONS IN AXIAL DIRECTION | 0.286 | 0.319 | 0.376 | 0.398 | 0.348 |
| | THE NUMBER OF ORIENTATION DISTRIBUTIONS IN CIRCUMFERENTIAL DIRECTION | 0.458 | 0.512 | 0.489 | 0.444 | 0.377 |
| PROXIMAL PORTION (P₃) | THE NUMBER OF ORIENTATION DISTRIBUTIONS IN THICKNESS DIRECTION | 0.232 | 0.149 | 0.123 | 0.145 | 0.266 |
| | THE NUMBER OF ORIENTATION DISTRIBUTIONS IN AXIAL DIRECTION | 0.263 | 0.299 | 0.364 | 0.386 | 0.339 |
| | THE NUMBER OF ORIENTATION DISTRIBUTIONS IN CIRCUMFERENTIAL DIRECTION | 0.505 | 0.552 | 0.514 | 0.468 | 0.395 |
| THE NUMBER OF ORIENTATION DISTRIBUTIONS IN CIRCUMFERENTIAL DIRECTION | Max (%) | 50.5 | 55.2 | 51.4 | 46.8 | 39.5 |
| | Min (%) | 45.8 | 51.2 | 48.9 | 44.4 | 37.7 |
| | σ (%) | 2.4 | 2.2 | 1.3 | 1.2 | 1.0 |
| | Max-Min (%) | 4.7 | 4.1 | 2.4 | 2.4 | 1.8 |
| THE NUMBER OF ORIENTATION DISTRIBUTIONS IN AXIAL DIRECTION | Max (%) | 28.6 | 31.9 | 37.6 | 39.8 | 34.8 |
| | Min (%) | 26.3 | 29.9 | 36.4 | 38.6 | 33.9 |
| | σ (%) | 1.2 | 1.1 | 0.7 | 0.6 | 0.5 |
| | Max-Min (%) | 2.4 | 2.0 | 2 | 1.2 | 0.9 |
| THE NUMBER OF ORIENTATION DISTRIBUTIONS IN THICKNESS DIRECTION | Max (%) | 25.6 | 16.9 | 13.5 | 15.8 | 27.5 |
| | Min (%) | 23.2 | 14.9 | 12.3 | 14.5 | 26.6 |
| | σ (%) | 1.2 | 1.1 | 0.7 | 0.6 | 0.5 |
| | Max-Min (%) | 2.4 | 2.0 | 1.2 | 1.2 | 0.9 |

FIG. 19

| | | INNER LAYER | INTERMEDIATE LAYER | | | OUTER LAYER |
|---|---|---|---|---|---|---|
| | | | INNER INTERFACE | CENTER | OUTER INTERFACE | |
| DISTAL PORTION (P₁) | THE NUMBER OF ORIENTATION DISTRIBUTIONS IN THICKNESS DIRECTION | 0.247 | 0.165 | 0.138 | 0.153 | 0.271 |
| | THE NUMBER OF ORIENTATION DISTRIBUTIONS IN AXIAL DIRECTION | 0.260 | 0.291 | 0.361 | 0.420 | 0.361 |
| | THE NUMBER OF ORIENTATION DISTRIBUTIONS IN CIRCUMFERENTIAL DIRECTION | 0.492 | 0.544 | 0.500 | 0.426 | 0.369 |
| CENTER (P₂) | THE NUMBER OF ORIENTATION DISTRIBUTIONS IN THICKNESS DIRECTION | 0.253 | 0.173 | 0.145 | 0.161 | 0.270 |
| | THE NUMBER OF ORIENTATION DISTRIBUTIONS IN AXIAL DIRECTION | 0.266 | 0.299 | 0.368 | 0.428 | 0.360 |
| | THE NUMBER OF ORIENTATION DISTRIBUTIONS IN CIRCUMFERENTIAL DIRECTION | 0.481 | 0.528 | 0.488 | 0.411 | 0.370 |
| PROXIMAL PORTION (P₃) | THE NUMBER OF ORIENTATION DISTRIBUTIONS IN THICKNESS DIRECTION | 0.246 | 0.157 | 0.135 | 0.153 | 0.265 |
| | THE NUMBER OF ORIENTATION DISTRIBUTIONS IN AXIAL DIRECTION | 0.259 | 0.283 | 0.359 | 0.421 | 0.355 |
| | THE NUMBER OF ORIENTATION DISTRIBUTIONS IN CIRCUMFERENTIAL DIRECTION | 0.495 | 0.560 | 0.506 | 0.426 | 0.380 |
| THE NUMBER OF ORIENTATION DISTRIBUTIONS IN CIRCUMFERENTIAL DIRECTION | Max (%) | 49.5 | 56.0 | 50.6 | 42.6 | 38.0 |
| | Min (%) | 48.1 | 52.8 | 48.8 | 41.1 | 36.9 |
| | σ (%) | 0.7 | 1.6 | 1.0 | 0.9 | 0.6 |
| | Max-Min (%) | 1.3 | 3.1 | 1.9 | 1.5 | 1.1 |
| THE NUMBER OF ORIENTATION DISTRIBUTIONS IN AXIAL DIRECTION | Max (%) | 26.6 | 29.9 | 36.8 | 42.8 | 36.1 |
| | Min (%) | 25.9 | 28.3 | 35.9 | 42.0 | 35.5 |
| | σ (%) | 0.4 | 0.8 | 0.5 | 0.4 | 0.3 |
| | Max-Min (%) | 0.7 | 1.6 | 0.9 | 0.8 | 0.6 |
| THE NUMBER OF ORIENTATION DISTRIBUTIONS IN THICKNESS DIRECTION | Max (%) | 25.3 | 17.3 | 14.5 | 16.1 | 27.1 |
| | Min (%) | 24.6 | 15.7 | 13.5 | 15.3 | 26.5 |
| | σ | 0.4 | 0.8 | 0.5 | 0.4 | 0.3 |
| | Max-Min | 0.7 | 1.6 | 0.9 | 0.8 | 0.6 |

FIG. 20

|  | EXAMPLE 3 | EXAMPLE 4 |
|---|---|---|
| AVERAGE BURST PRESSURE (atm) | 29.1 | 29.7 |
| MAXIMUM BURST PRESSURE (atm) | 30.0 | 31.0 |
| MINIMUM BURST PRESSURE (atm) | 25.0 | 28.0 |
| $\sigma$ | 1.14 | 0.94 |
| RATED BURST PRESSURE (RBP) (atm) | 24.5 | 25.9 |

BALLOON AND METHOD OF MANUFACTURING THE SAME

CROSS-REFERENCES TO RELATED APPLICATION

This application is a continuation of International Application No. PCT/JP2013/056793 filed on Mar. 12, 2013, the entire content of which is incorporated herein by reference.

TECHNICAL FIELD

The present invention relates to a balloon and a method of manufacturing the same.

BACKGROUND DISCUSSION

In a balloon catheter, a dilatable balloon is installed at a distal end portion thereof. For example, the balloon catheter is used in order to dilate a stenosed portion or an obstructive portion so as to improve blood flow when stenosis or obstruction occurs in a blood vessel. The balloon has been configured to have strength and shock resistance able to withstand an increase of internal pressure when a target portion is dilated.

However, there exists the possibility of breakage of a balloon caused by an unexpected rapid increase of internal pressure or a shock due to unexpected contact with biological tissue which is hardened, that is, calcified, for example. A rupture in a circumferential direction and a rupture in an axial direction are assumed when there is a breakage of the balloon. Different from the rupture in the axial direction, a fragment separated from the balloon is likely to occur in the rupture in the circumferential direction. Therefore, there is an increased need to prevent the rupture in the circumferential direction from occurring.

SUMMARY

The disclosure herein has been made in order to solve the problem entailed in the conventional technology by providing a balloon in which the rupture in the circumferential direction can be prevented from occurring, and a method of manufacturing the same.

The disclosure is directed to a balloon which is arranged on a medical catheter including: a dilatable cylindrical portion that is formed with a birefringent polymer material, in which a ratio of the number of orientation distributions, calculated by dividing the number of orientation distributions of the cylindrical portion in a circumferential direction by the number of orientation distributions of the cylindrical portion in an axial direction, is less than 2.

Another aspect of the disclosure is directed to a method of manufacturing a balloon which is arranged on a medical catheter including a molding step of performing blow molding of a tubular parison which is formed with a birefringent polymer material and molding a dilatable cylindrical portion of the balloon, in which in the molding step, the cylindrical portion is molded so as to cause a ratio of the number of orientation distributions, calculated by dividing the number of orientation distributions of the cylindrical portion in a circumferential direction by the number of orientation distributions of the cylindrical portion in an axial direction, to be less than 2.

According to an exemplary embodiment of the disclosure, a balloon, in which a ratio of the number of orientation distributions calculated by dividing the number of orientation distributions of a cylindrical portion in a circumferential direction by the number of orientation distributions of the cylindrical portion in an axial direction is less than 2, has a physical property in which a rupture in the circumferential direction can be prevented. In other words, it is possible to provide a balloon in which the rupture in the circumferential direction can be prevented from occurring, and a method of manufacturing the same.

As necessary, the balloon (the cylindrical portion) can have a multi-layer structure made with polymer materials which are different from each other.

It is preferable that fluctuation in the axial direction in the ratio of the number of orientation distributions in a layer having the maximum strength is 1 or less in terms of a standard deviation. In this case, pressure resistance can be improved.

A medical catheter is a balloon catheter, for example. The balloon catheter can also be applied to a stent delivery system for causing a stent to indwell inside a human body.

When a molding step includes a stretching step in which a heated tubular parison is expanded by pressure applied to the inside of the tubular parison while the heated tubular parison is stretched in the axial direction, the cylindrical portion can be molded so as to cause the ratio of the number of orientation distributions to be less than 2 by controlling a stretching speed.

In the stretching step, when stretching is ceased the moment the expanded tubular parison comes into contact with a cavity surface of a blow molding die, abrasion caused by the expanded tubular parison grazing against the cavity surface can be prevented from occurring.

When a tubular parison having the multi-layer structure made with the polymer materials which are different from each other is applied, it is possible to obtain a balloon (the cylindrical portion) having the multi-layer structure.

Other characteristics and properties of the disclosure will become clear with reference to preferable embodiments exemplified in the following descriptions and accompanying drawings.

BRIEF DESCRIPTION OF THE DRAWINGS

FIG. 16 is a table showing relationships between a ratio of the number of orientation distributions and a rupture in the circumferential direction in Examples 1 and 2, and Comparison Examples 1 to 5.

FIG. 18 is a table for illustrating fluctuation in the numbers of orientation distributions in Example 3.

FIG. 19 is a table for illustrating fluctuation in the numbers of orientation distributions in Example 4.

FIG. 20 is a table for illustrating pressure resistance data of Examples 3 and 4.

DETAILED DESCRIPTION

Figure 1:
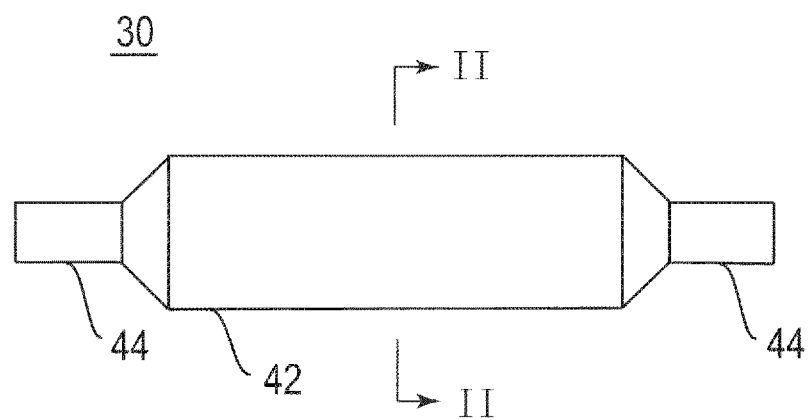
FIG. 1 is a side view illustrating a balloon according to an exemplary embodiment of the disclosure.
Figure 2:
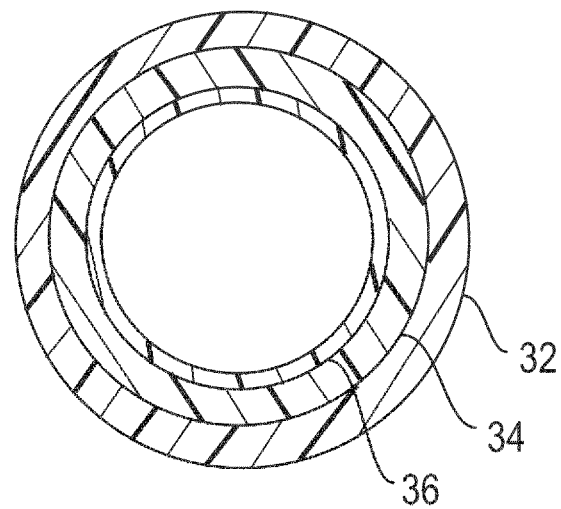
FIG. 2 is a cross-sectional view taken along line II-II in FIG. 1.
Figure 3:
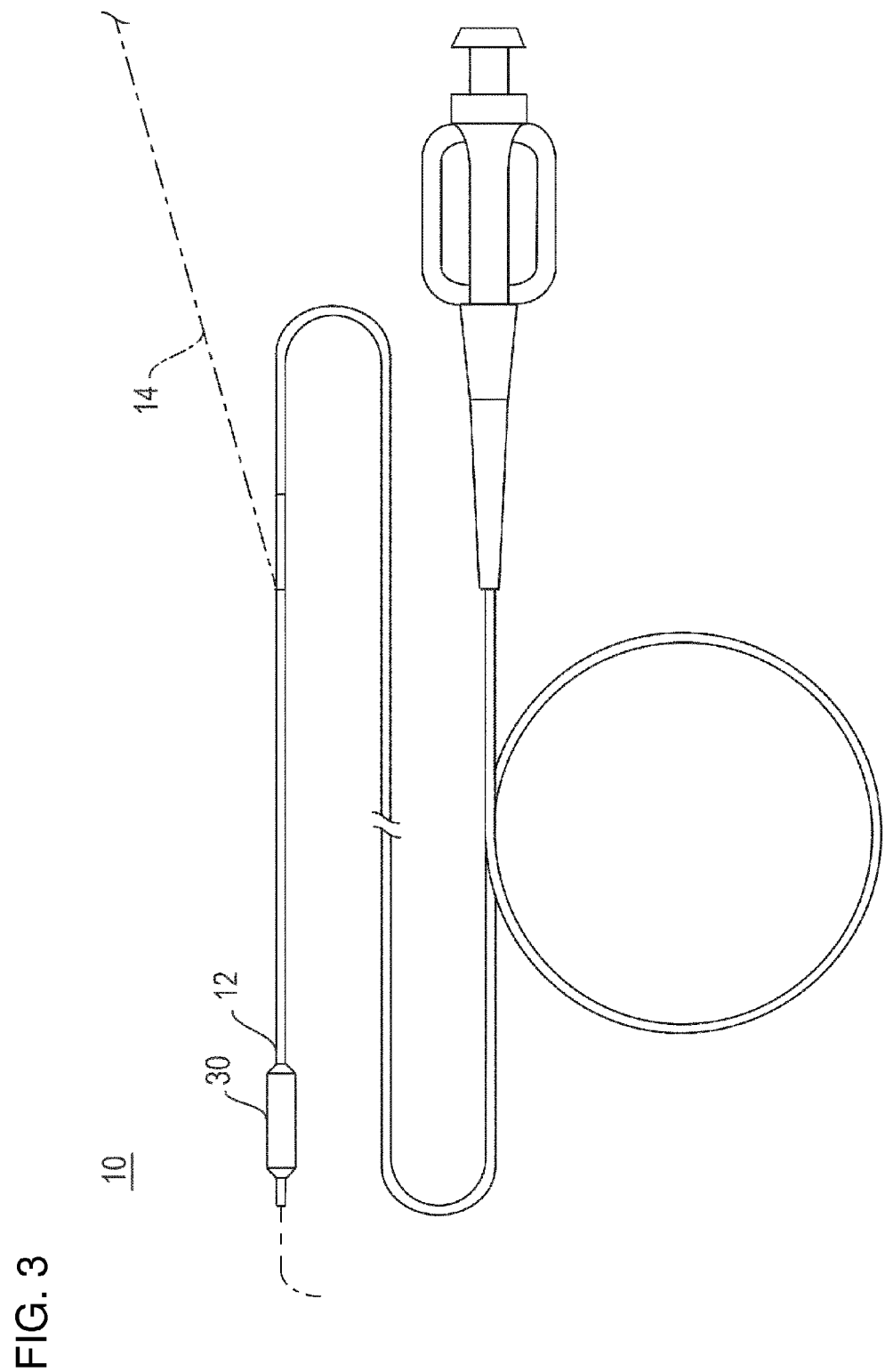
FIG. 3 is a schematic diagram for illustrating a medical catheter including the balloon shown in FIG. 1.
Figure 4:
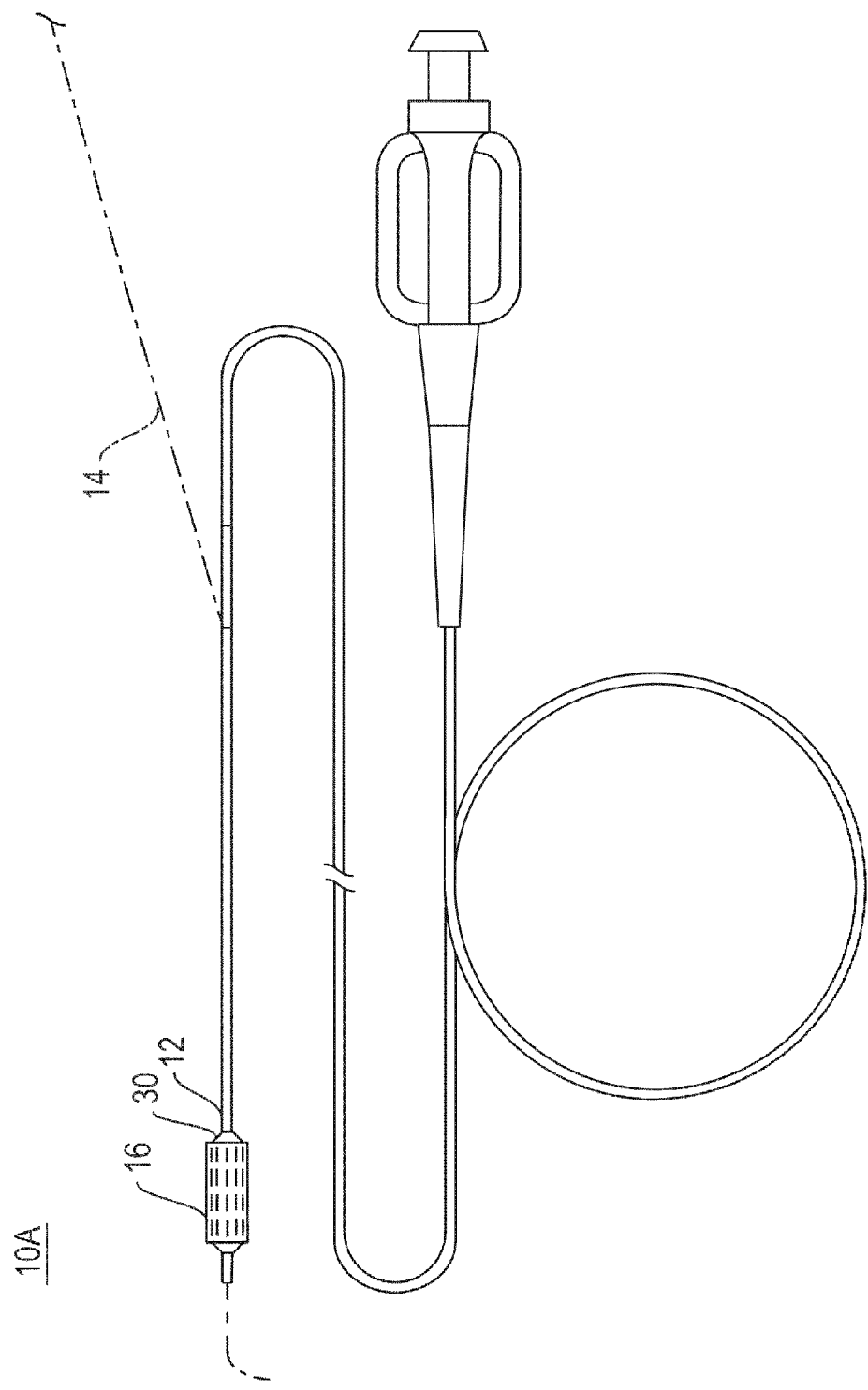
FIG. 4 is a schematic diagram for illustrating another form of a medical catheter including the balloon shown in FIG. 1.

FIG. 1 is a side view illustrating a balloon according to an exemplary embodiment of the disclosure herein. FIG. 2 is a cross-sectional view taken along line II-II in FIG. 1. FIG. 3 is a schematic diagram for illustrating a medical catheter including the balloon shown in FIG. 1. FIG. 4 is a schematic diagram for illustrating another form of a medical catheter including the balloon shown in FIG. 1.

A balloon 30 according to an exemplary embodiment of the disclosure is applied to a balloon catheter 10 as shown in FIG. 3, for example. The balloon catheter 10 is a medical catheter which is utilized for treatment of a portion where surgery cannot be easily performed, treatment aimed at being minimally invasive with respect to a human body, a cardiovascular contrast examination, or the like. The treatment of a portion where surgery cannot be easily performed is percutaneous transluminal coronary angioplasty (PTCA) which is applied to myocardial infarction and angina pectoris, for example. The balloon catheter 10 is not limited to a form applied to a stenosed portion which occurs in a cardiac coronary artery. The balloon catheter 10 can be applied to a stenosed portion which occurs in other blood vessels, the bile duct, the trachea, the esophagus, the urethra, or the like.

The balloon catheter 10 is a rapid exchange (RX) type having a structure in which a guide wire 14 passes through only a distal portion. The balloon catheter 10 includes a distal shaft 12 to which the balloon 30 is connected in a state where fluid tightness is maintained. The distal shaft 12 has a lumen for introducing a balloon dilation fluid.

As illustrated in FIG. 1, the balloon 30 includes a cylindrical portion 42, and tapered portions 44 positioned on both sides of the cylindrical portion 42. As illustrated in FIG. 2, the balloon 30 exhibits a three-layer structure including an outer layer 32, an intermediate layer 34, and an inner layer 36. The cylindrical portion 42 has been configured to be dilatable by the balloon dilation fluid which is introduced via the lumen of the distal shaft 12.

The cylindrical portion 42 has a physical property in which a rupture in a circumferential direction can be prevented. As described below, the aforementioned physical property is a ratio of the number of orientation distributions, which is calculated by dividing the number of orientation distributions of the cylindrical portion 42 in the circumferential direction by the number of orientation distributions of the cylindrical portion 42 in an axial direction (a ratio of the number of orientation distributions of the cylindrical portion 42 in the circumferential direction to the number of orientation distributions of the cylindrical portion 42 in the axial direction), and the ratio is calculated based on a refractive index and intrinsic birefringence of a balloon forming material.

The outer diameter of the cylindrical portion 42 while being dilated is set to range from 1.0 mm to 10 mm, and is preferably set to range from 1.0 mm to 5.0 mm. The length of the cylindrical portion 42 ranges from 5 mm to 50 mm, and preferably ranges from 10 mm to 40 mm. The overall length of the balloon 30 ranges from 10 mm to 200 mm, and preferably ranges from 20 mm to 40 mm.

The balloon forming material is a polymer material such as, for example, polyolefin, a cross-linked body of polyolefin, polyester, a polyester elastomer, polyvinyl chloride, polyurethane, a polyurethane elastomer, polyphenylene sulfide, polyamide, a polyamide elastomer, a fluorine resin, and the like; silicone rubber; and latex rubber. A preferred polyester is, for example, polyethylene terephthalate.

Polyamide is not particularly limited as long as the polyamide is a polymer having an amide bond. For example, the polyamide is a homopolymer such as polycaprolactam (nylon 6), polyhexamethylene adipamide (nylon 66), polyundecanolactam (nylon 11), polydodecanolactam (nylon 12), and the like. For example, the polyamide elastomer is a block copolymer having nylon 6, nylon 66, nylon 11, nylon 12, or the like as a hard segment, and having polyalkylene glycol, polytetramethylene ether glycol, polyether, aliphatic polyester, or the like as a soft segment.

In the exemplary embodiment, from a viewpoint of appropriate balance between flexibility and strength, the outer layer 32 and the inner layer 36 are formed of a polyamide elastomer having polyamide 12 (nylon 12) and polytetramethylene ether glycol as a hard segment and a soft segment, and the intermediate layer 34 is formed of polyamide 12.

The balloon 30 is not limited to a form having the three-layer structure. The balloon 30 can have a single (single layer) structure, a two-layer structure, or a structure of four or more layers.

The medical catheter applied with the balloon 30 is not limited to the balloon catheter 10. For example, it is possible to apply the balloon 30 to a stent delivery system 10A as shown in FIG. 4. The stent delivery system 10A has a stent 16 which is arranged on the outer circumference of the balloon 30. The stent delivery system 10A is applied to treatment aimed at preventing restenosis after performing percutaneous transluminal coronary angioplasty (PTCA), for example.

The stent 16 is a substance indwelling inside a living body for retaining a lumen by coming into close contact with the inner surface of a stenosed portion so as to indwell therein. The stent 16 has been configured to be expandable. The balloon 30 is configured to expand the stent 16 which is arranged on the outer circumference thereof so as to increase in diameter. The stent 16 is formed with a material having biocompatibility such as, for example, a nickel-titanium alloy, a cobalt-chromium alloy, stainless steel, iron, titanium, aluminum, tin, and a zinc-tungsten alloy.

Subsequently, detailed descriptions will be given regarding a method of calculating the number of orientation distributions in the circumferential direction and the number of orientation distributions in the axial direction related to a physical property in which the rupture in the circumferential direction can be prevented.

Figure 5:
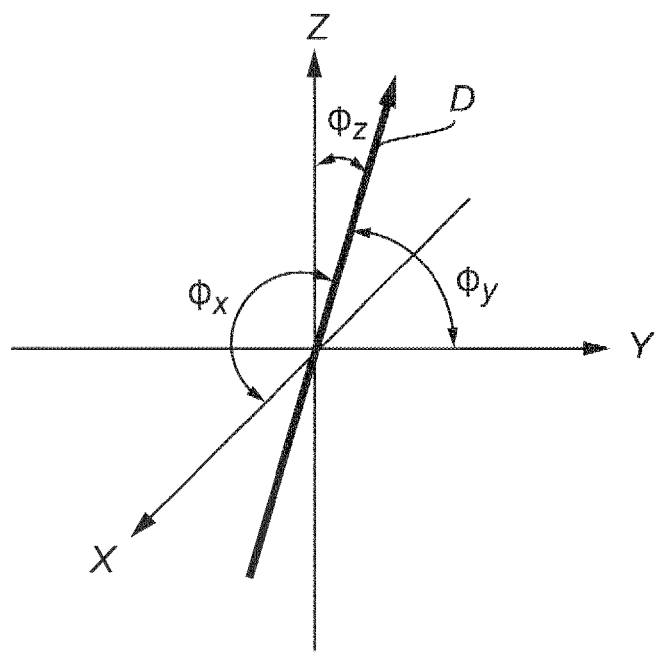
FIG. 5 is a graph for illustrating an intersection angle between an orientation direction and an X-axis, an intersection angle between the orientation direction and a Y-axis, and an intersection angle between the orientation direction and a Z-axis.
Figure 6:
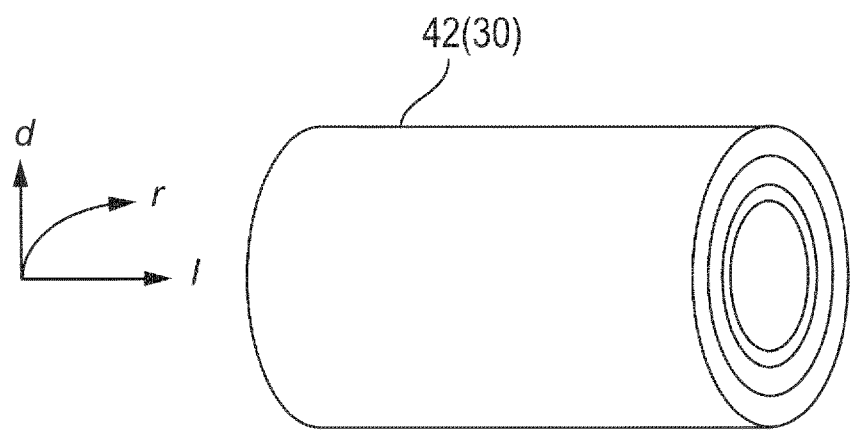
FIG. 6 is a graph for illustrating a circumferential direction, a thickness direction, and an axial direction of a cylindrical portion of the balloon.

FIG. 5 is a graph for illustrating an intersection angle between an orientation direction and an X-axis, an intersection angle between the orientation direction and a Y-axis, and an intersection angle between the orientation direction and a Z-axis. FIG. 6 is a graph for illustrating a circumferential direction, a thickness direction, and an axial direction of a cylindrical portion of the balloon.

When a rupture of the cylindrical portion of the balloon occurs due to ductile fracture, breaking stress is correlated with the number of molecular chains (the number of orientation distributions) per unit sectional area of the balloon forming material. A ratio between an occurrence of the rupture in the circumferential direction and an occurrence of the rupture in the axial direction is affected by the number of orientation distributions. The number of orientation distributions is related to anisotropy of polarizability, and the anisotropy of polarizability is related to anisotropy of refractive index (optical anisotropy). Accordingly, the number of orientation distributions can be measured by utilizing a phenomenon of birefringence.

For example, when light is incident on an optical isomer, the light is divided into two refracted lights oscillating in directions perpendicular to each other. Therefore, the number of orientation distributions is analyzed by measuring a difference (a degree of birefringence) between the two refracted lights and calculating a refractive index. A comparison in terms of refractive index can be applied to a comparison of orientations under the same material and the same condition, but it is not suitable for a comparison between different types of resins. Therefore, in the exemplary embodiment of the disclosure, a definition is given regarding the physical property in which the rupture in the circumferential direction can be prevented by using the ratio of the number of orientation distributions.

Specifically, as illustrated in FIG. 5, an intersection angle between an orientation direction D and the X-axis, an intersection angle between the orientation direction D and the Y-axis, and an intersection angle between the orientation direction D and the Z-axis are respectively indicated as $\phi_x$, $\phi_y$, and $\phi_z$. The number of orientation distributions in the circumferential direction, the number of orientation distributions in the axial direction, and the number of orientation distributions in the thickness direction are thus defined by the following Expressions.

Expressions 1

$$\overline{\cos^2 \phi_x} + \overline{\cos^2 \phi_y} + \overline{\cos^2 \phi_z} = 1 \quad (1)$$

$$\overline{\cos^2 \phi_x} = n_z + \overline{\cos^2 \phi_y} \quad (2)$$

$$\overline{\cos^2 \phi_z} = n_x + \overline{\cos^2 \phi_y} \quad (3)$$

$$(1 - n_x - n_z)/3 = \overline{\cos^2 \phi_y} \quad (4)$$

In the above Expressions, $\overline{\cos^2 \phi_x}$ indicates the number of orientation distributions in the circumferential direction, $\overline{\cos^2 \phi_y}$ indicates the number of orientation distributions in the thickness direction, and $\overline{\cos^2 \phi_z}$ indicates the number of orientation distributions in the axial direction.

As illustrated in FIG. 6, when refractive index in a circumferential direction r, refractive index in a thickness direction d, and refractive index in an axial direction l are respectively indicated as nr, nd, and nl, $n_x$ and $n_z$ required for calculating the number of orientation distributions in the circumferential direction, the number of orientation distributions in the axial direction, and the number of orientation distributions in the thickness direction are calculated by the following Expressions 2 by utilizing intrinsic refringence $\Delta n^*$ which is a value of birefringence shown when molecules are oriented 100%. For example, refractive index is calculated by measuring retardation (a phase difference) using a polarizing microscope.

Expressions 2

$$n_z = |\Delta n \text{ length}|/\Delta n^* \quad (5)$$

$$n_x = |\Delta n \text{ axis}|/\Delta n^* \quad (6)$$

$$|\Delta n \text{ length}| = |nl - nd| \quad (7)$$

$$|\Delta n \text{ axis}| = |nr - nd| \quad (8)$$

$$n^2 = (nr^2 + nd^2 + nl^2)/3 \quad (9)$$

In the above Expressions, $n^2$ indicates average refractive index.

Figure 7:
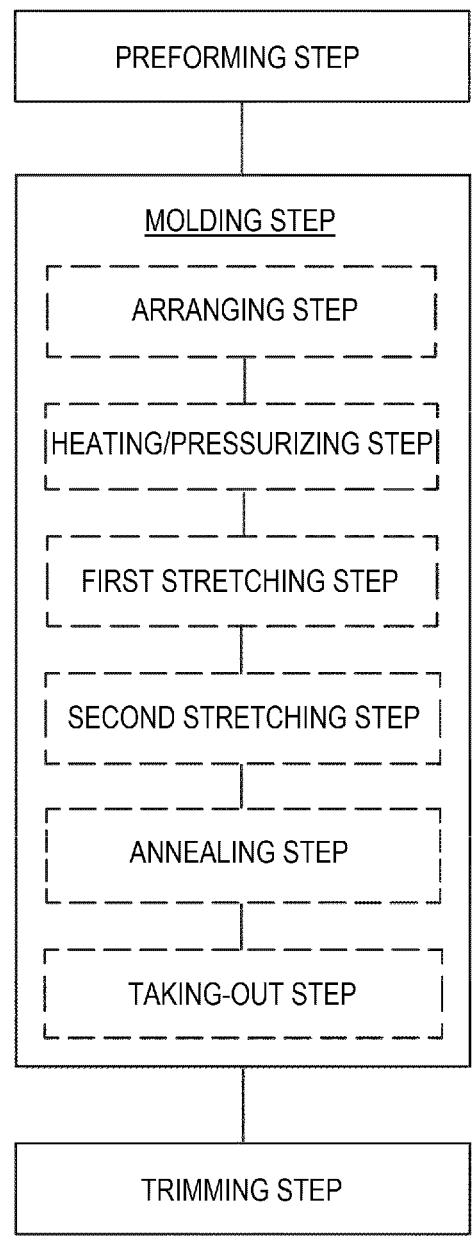
FIG. 7 is a flow chart for illustrating a method of manufacturing a balloon according to an exemplary embodiment of the disclosure.

FIG. 7 is a flow chart for illustrating the method of manufacturing a balloon according to the exemplary embodiment of the disclosure.

As illustrated in FIG. 7, the method of manufacturing a balloon according to the exemplary embodiment of the disclosure includes a preforming step, a molding step, and a trimming step.

In the preforming step, for example, a tubular parison (which comprises a material (preform) of the balloon 30 and has a three-layer structure) is molded through coextrusion.

The molding step includes an arranging step, a heating/pressurizing step, a first stretching step, a second stretching step, an annealing step, and a taking-out step. By performing blow molding, the tubular parison is molded into a shape which substantially coincides with the outer shape of the balloon 30.

In the trimming step, for example, an end portion of the molded tubular parison is cut, thereby obtaining the balloon 30.

Figure 8:
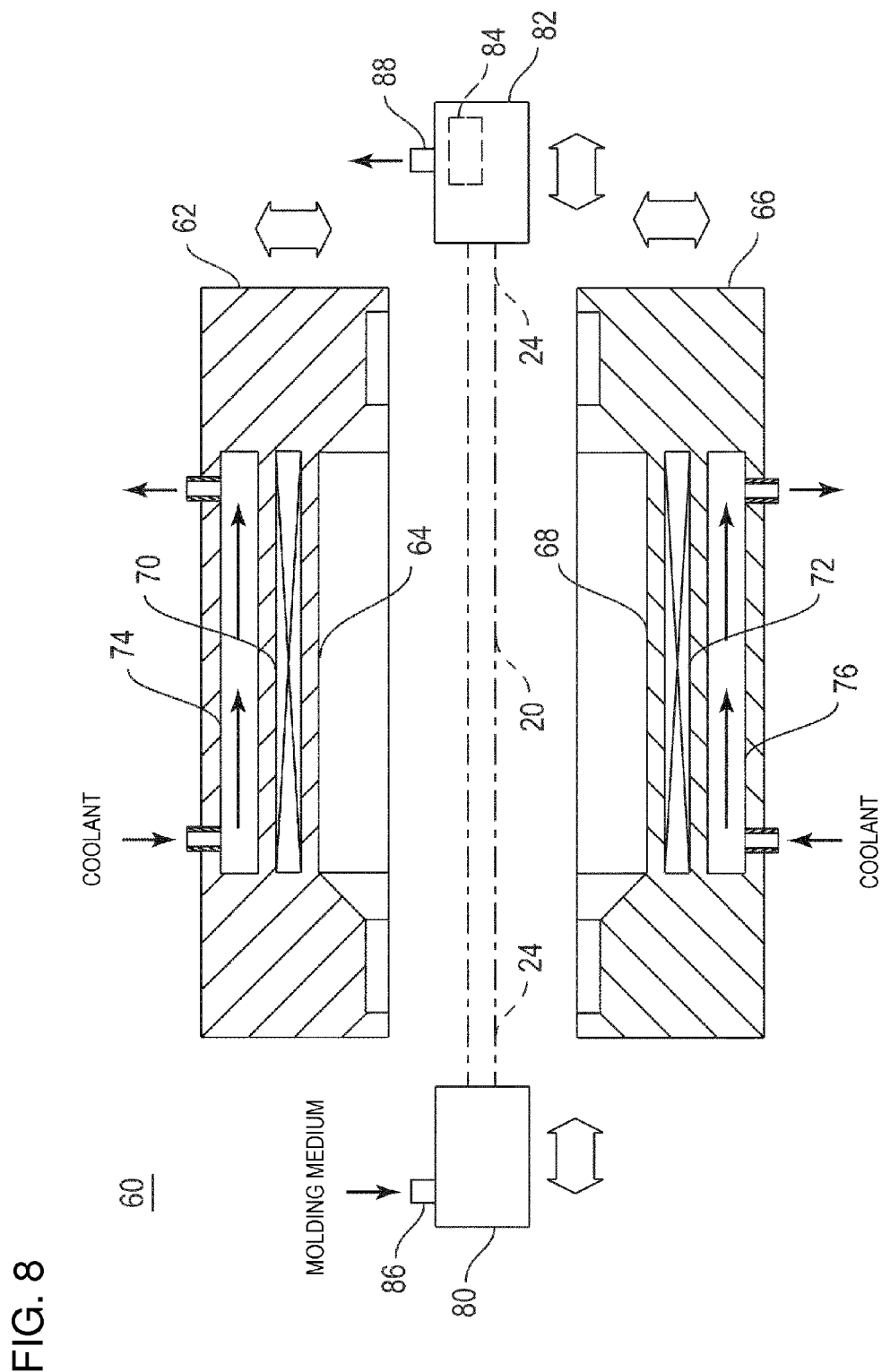
FIG. 8 is a cross-sectional view for illustrating a blow molding apparatus which is applied in a molding step shown in FIG. 7.

FIG. 8 is a cross-sectional view for illustrating a blow molding apparatus which may be utilized in the molding step shown in FIG. 7.

A blow molding apparatus 60 includes molding dies (blow molding dies) 62 and 66, and chuck portions 80 and 82. The molding dies 62 and 66 include cavity surfaces 64 and 68, heaters 70 and 72, and cooling jackets 74 and 76.

The cavity surfaces 64 and 68 integrally correspond to the outer shape of the balloon 30. When molding clamping of the molding dies 62 and 66 is performed, the cavity surfaces 64 and 68 exhibit the shapes which substantially coincide with the outer shape of the balloon 30.

The heaters 70 and 72 are formed with sheet heaters, for example, and are used for increasing temperatures of the molding dies 62 and 66 so as to indirectly heat a tubular parison 20 which is arranged in an internal space between the cavity surfaces 64 and 68, and increasing the temperature until the tubular parison 20 is plasticized.

The cooling jackets 74 and 76 are configured to be arranged on the outer circumference of the heaters 70 and 72 and allow a coolant to circulate therethrough. The coolant is used for indirectly cooling the tubular parison 20 which is arranged in the internal space between the cavity surfaces 64 and 68 by decreasing the temperatures of the molding dies 62 and 66. By way of example, the coolant is liquid such as water or the like, or gas such as air or the like.

The chuck portions 80 and 82 are arranged so as to be able to approach and be separated in the axial direction of the tubular parison 20. The chuck portions 80 and 82 are used for grasping an end portion 24 of the tubular parison 20. The chuck portion 80 includes an injection port 86, and the chuck portion 82 includes a load cell 84 and a discharge port 88. The injection port 86 is used for injecting a molding fluid into the tubular parison 20 so as to apply pressure to the inside of the tubular parison 20 (increase internal pressure). The discharge port 88 is used for discharging the molding fluid from the tubular parison 20 so as to return the inside of the tubular parison 20 to atmospheric pressure. The molding fluid may be air or nitrogen, for example.

Figure 9:
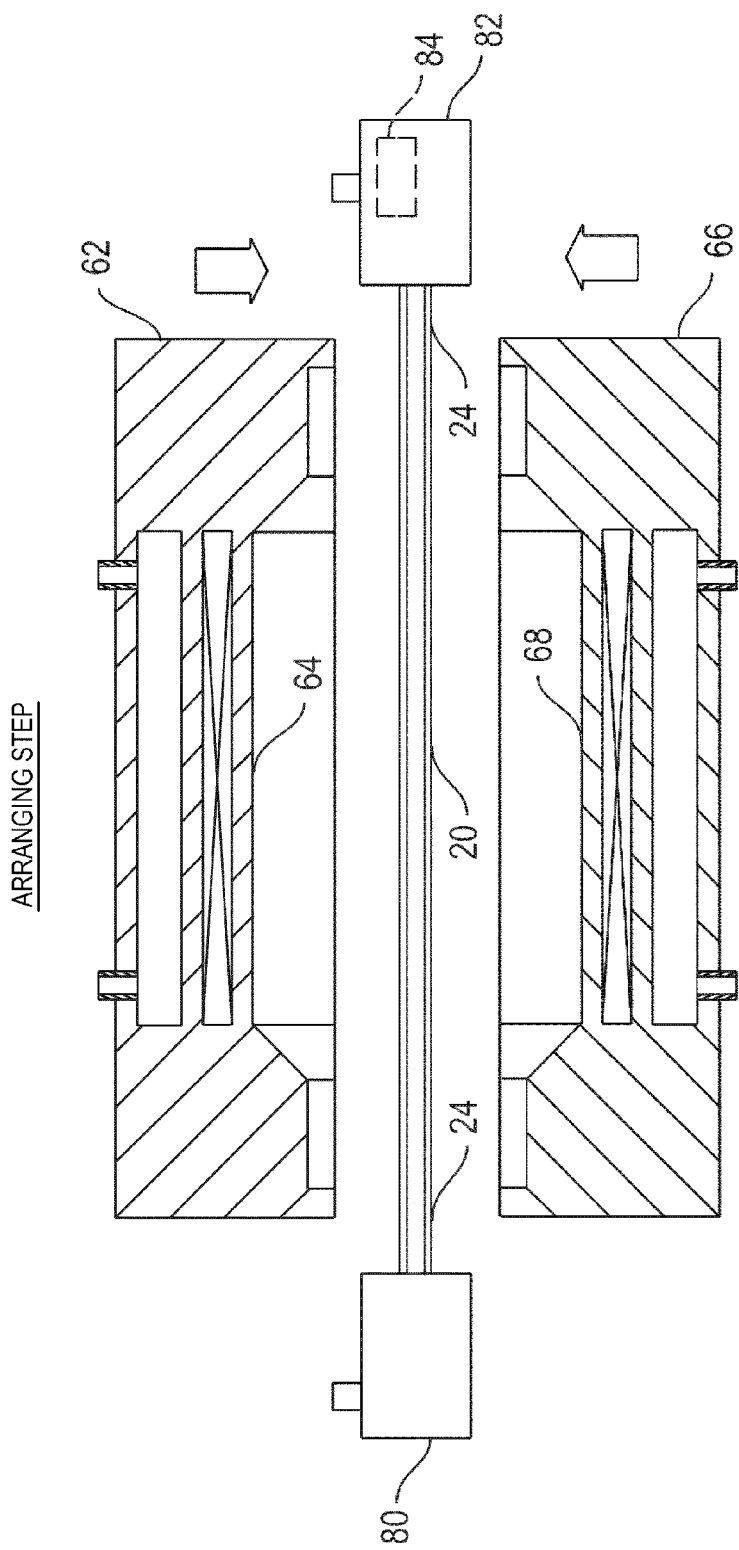
FIG. 9 is a cross-sectional view for illustrating an arranging step shown in FIG. 7.
Figure 10:
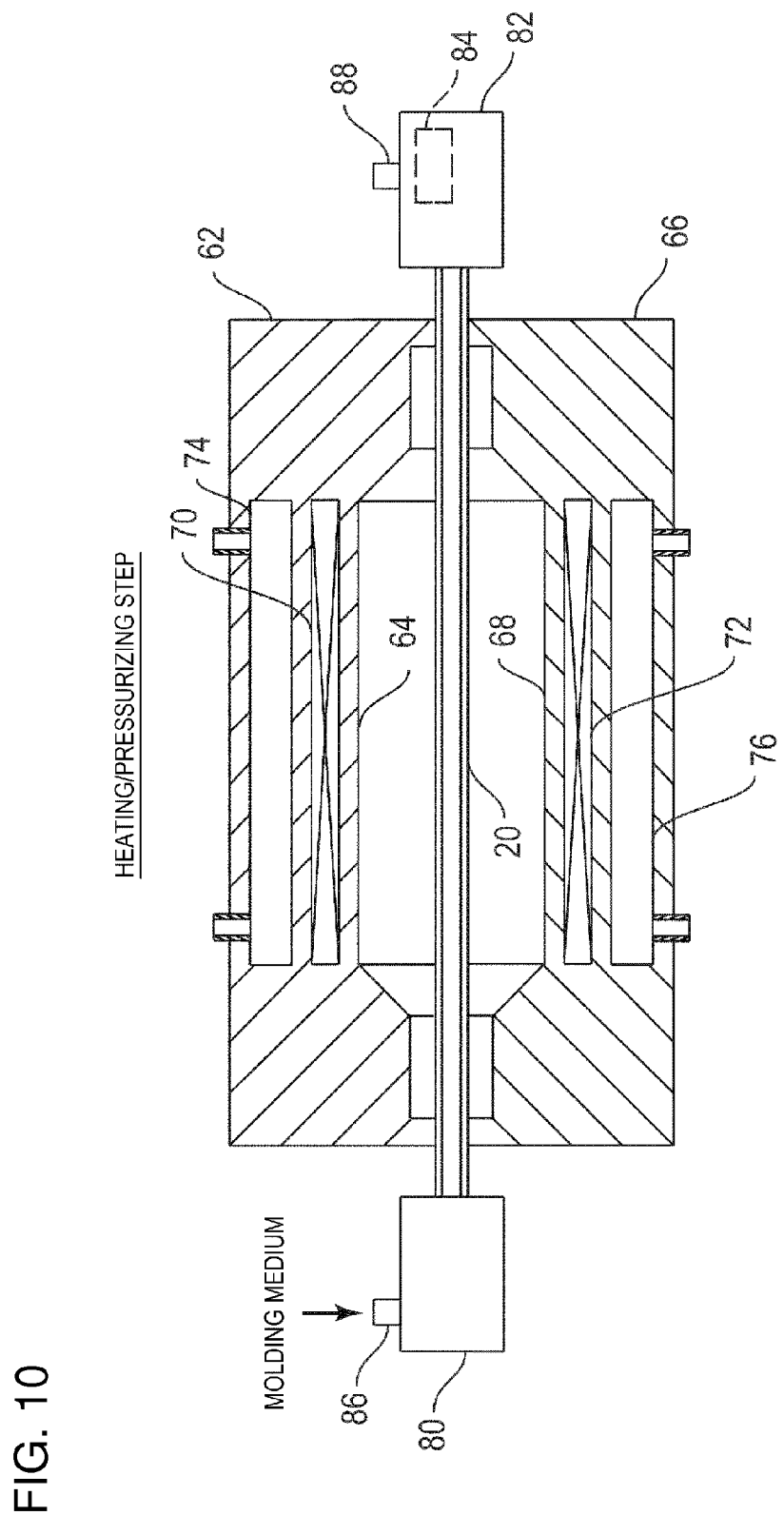
FIG. 10 is a cross-sectional view for illustrating a heating/pressurizing step shown in FIG. 7.
Figure 11:
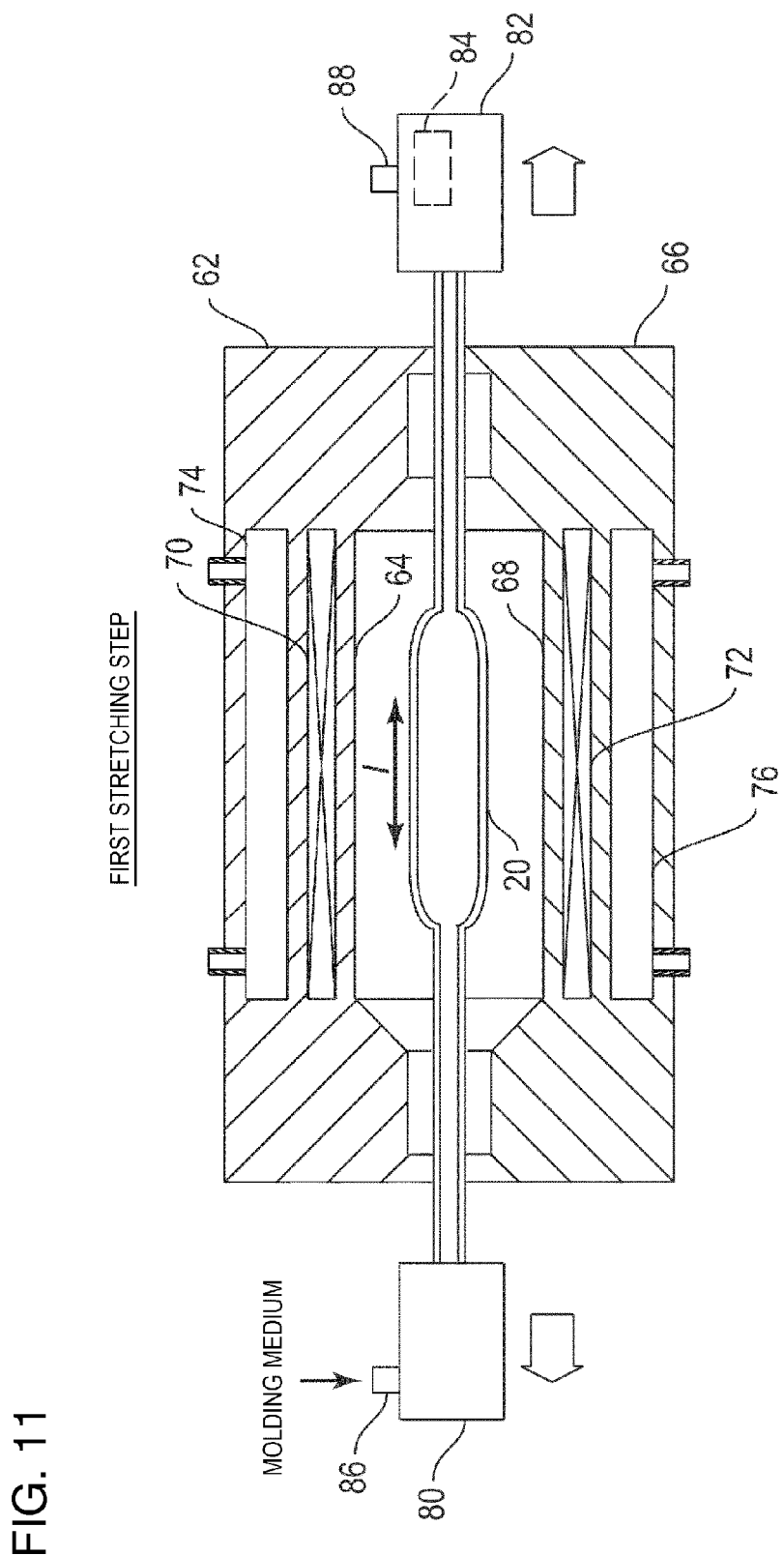
FIG. 11 is a cross-sectional view for illustrating a first stretching step shown in FIG. 7.
Figure 12:
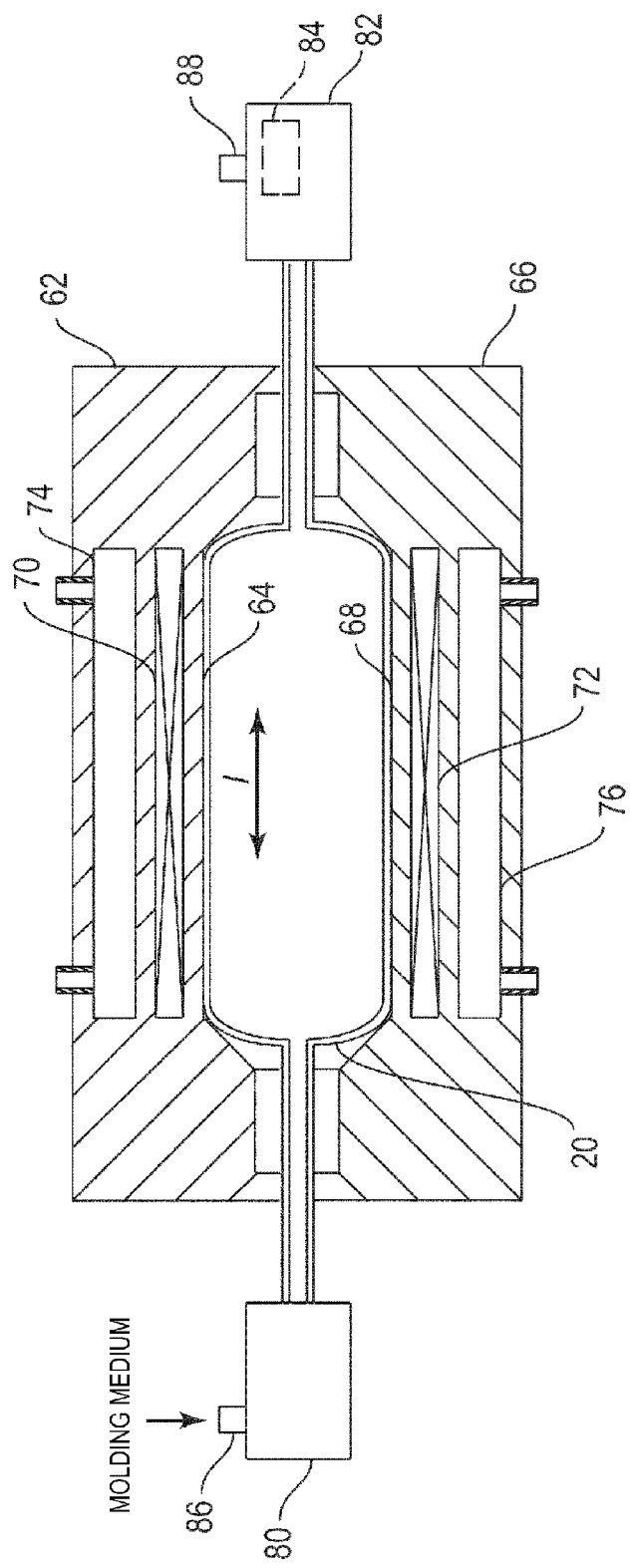
FIG. 12 is a cross-sectional view for illustrating the timing of cessation of stretching in the first stretching step.
Figure 13:
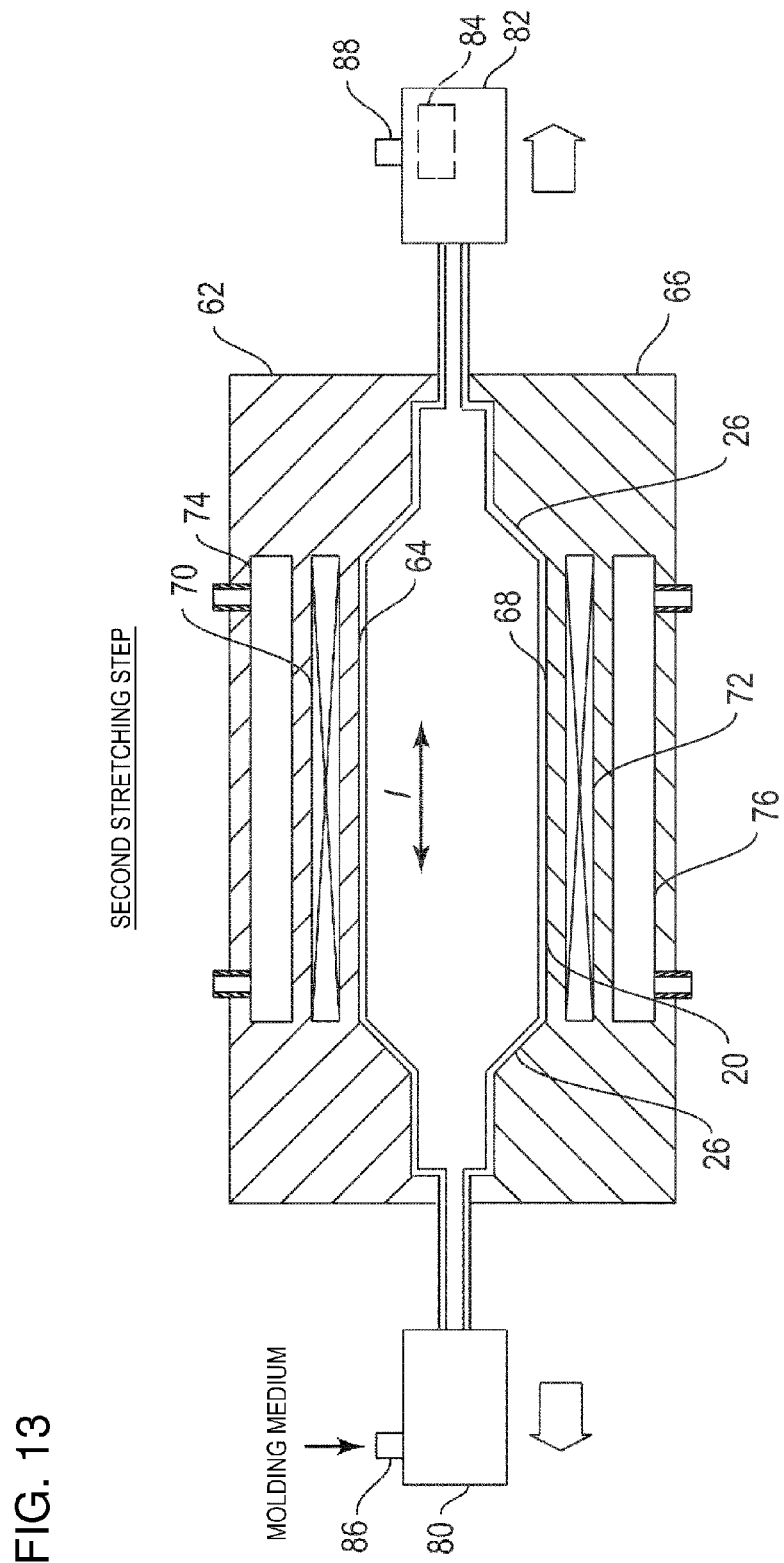
FIG. 13 is a cross-sectional view for illustrating a second stretching step shown in FIG. 7.
Figure 14:
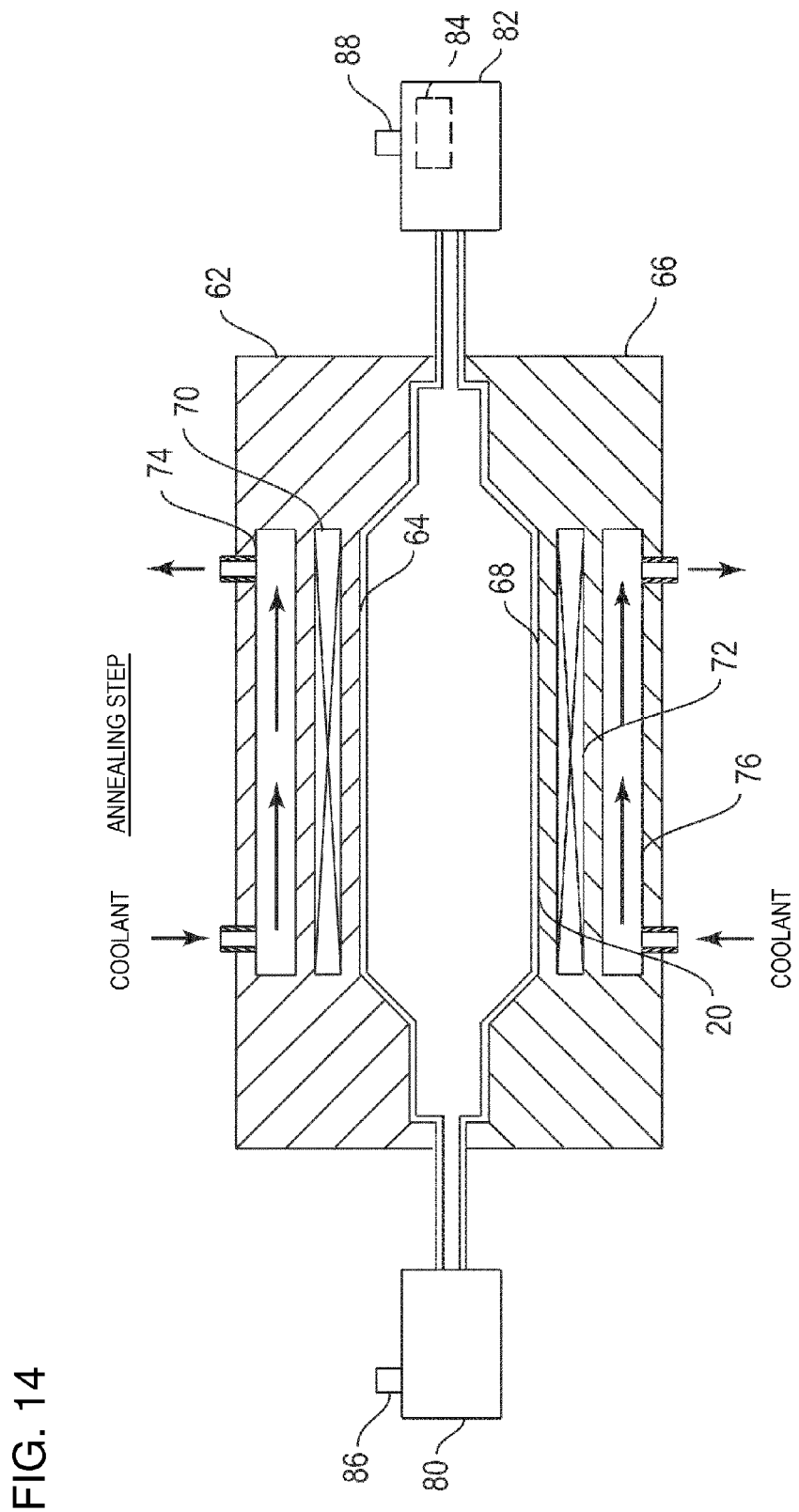
FIG. 14 is a cross-sectional view for illustrating an annealing step shown in FIG. 7.
Figure 15:
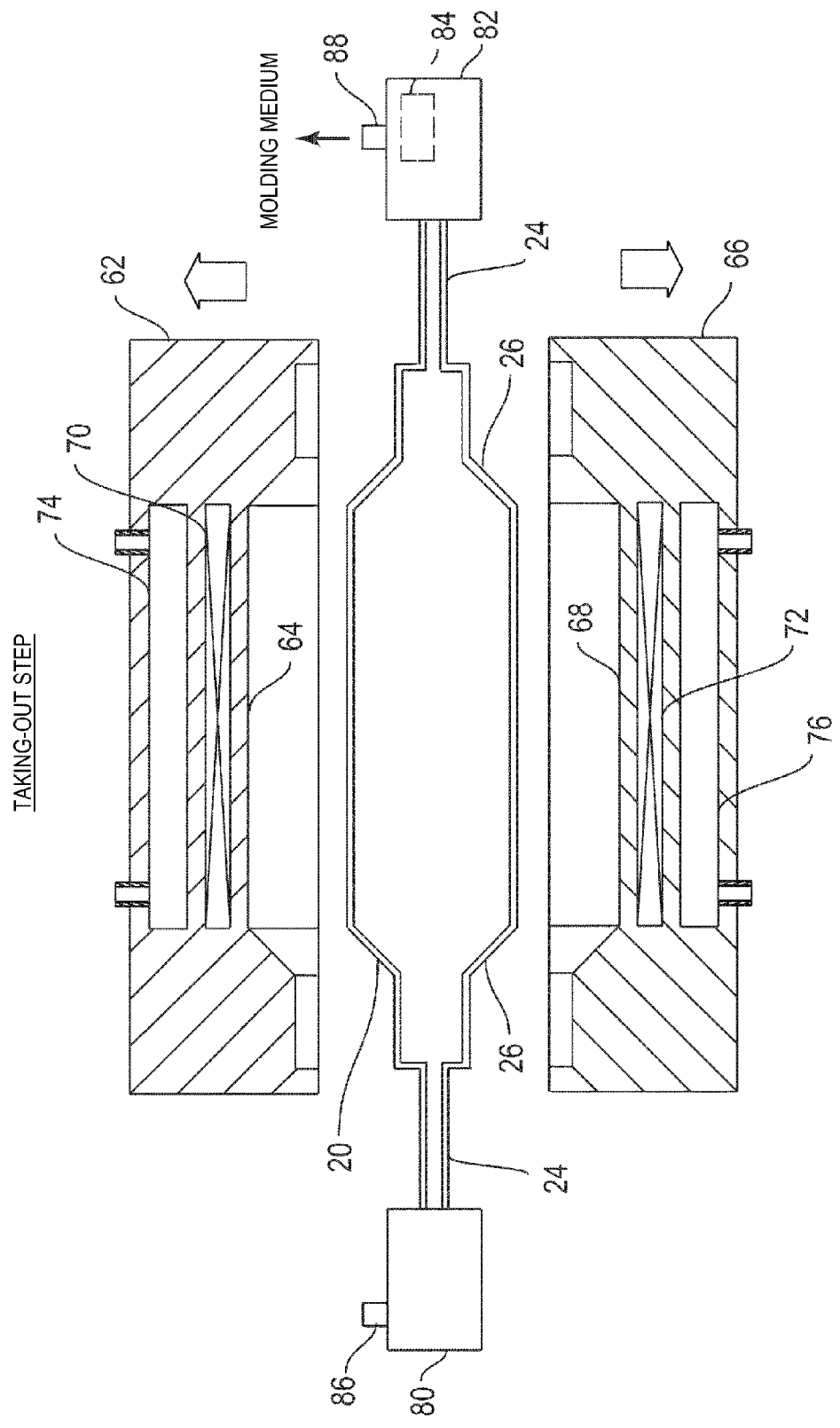
FIG. 15 is a cross-sectional view for illustrating a taking-out step shown in FIG. 7.

FIG. 9 is a cross-sectional view for illustrating the arranging step shown in FIG. 7. FIG. 10 is a cross-sectional view for illustrating the heating/pressurizing step shown in FIG. 7. FIG. 11 is a cross-sectional view for illustrating the first stretching step shown in FIG. 7. FIG. 12 is a cross-sectional view for illustrating the timing of cessation of stretching in the first stretching step. FIG. 13 is a cross-sectional view for illustrating the second stretching step shown in FIG. 7. FIG. 14 is a cross-sectional view for illustrating the annealing step shown in FIG. 7. FIG. 15 is a cross-sectional view for illustrating the taking-out step shown in FIG. 7. In FIGS. 9 to 15, the cross section of the tubular parison 20 is simplified, thereby being shown as a single layer.

In the arranging step, as illustrated in FIG. 9, the tubular parison 20 is held by the chuck portions 80 and 82, and is arranged in the internal space formed by the cavity surfaces 64 and 68 of the molding dies 62 and 66. Thereafter, molding clamping of the molding dies 62 and 66 is performed.

In the heating/pressurizing step, as illustrated in FIG. 10, the temperatures of the molding dies 62 and 66 are increased by operating the heaters 70 and 72 so as to indirectly heat the tubular parison 20 which is arranged in the internal space between the cavity surfaces 64 and 68. The temperature is increased until the tubular parison 20 is plasticized, and a molding medium is then introduced. The molding medium passes through the injection port 86 of the chuck portion 80 and is injected into the tubular parison 20. Hence, pressure is applied to the inside of the tubular parison 20 (internal pressure is increased).

In the first stretching step, as illustrated in FIG. 11, the chuck portions 80 and 82 grasping the end portions 24 of the tubular parison 20 are separated from each other, and the tubular parison 20 is expanded by pressure applied to the inside of the tubular parison 20 while stretching the tubular parison 20 in the axial direction "I". In this case, stretching is executed at a high speed, thereby strongly causing the orientation of the tubular parison 20 in the axial direction to be uniform. The speed of stretching is set to cause the ratio of the number of orientation distributions to be less than 2.

As illustrated in FIG. 12, stretching is ceased the moment the expanded tubular parison 20 comes into contact with the cavity surfaces 64 and 68. Accordingly, abrasion caused by grazing against the cavity surfaces 64 and 68 is prevented from occurring. The presence/absence of contact is determined by a load change which is detected by the load cell 84 arranged in the chucks 80 and 82.

In the second stretching step, as illustrated in FIG. 13, the chuck portions 80 and 82 are separated farther away from each other, the end portion of the tubular parison 20 is expanded by pressure applied to the inside of the tubular parison 20 while the tubular parison 20 is stretched in the axial direction "I", thereby forming a tapered portion 26.

In the annealing step, as illustrated in FIG. 14, heating performed by the heaters 70 and 72 is ceased, and thereafter the coolant is introduced into the cooling jackets 74 and 76. The coolant indirectly cools off the tubular parison 20 by decreasing the temperatures of the molding dies 62 and 66.

In the taking-out step, as illustrated in FIG. 15, the molding fluid is discharged from the discharge port 88 so as to return the inside of the tubular parison 20 to atmospheric pressure, and mold opening of the molding dies 62 and 66 is performed, thereby taking out the tubular parison 20. In this case, excluding the shape of the end portion 24, the tubular parison 20 has a shape which substantially coincides with the outer shape of the balloon 30, and as described above, the end portion 24 is cut in the following trimming step, thereby obtaining the balloon 30.

Figure 17:
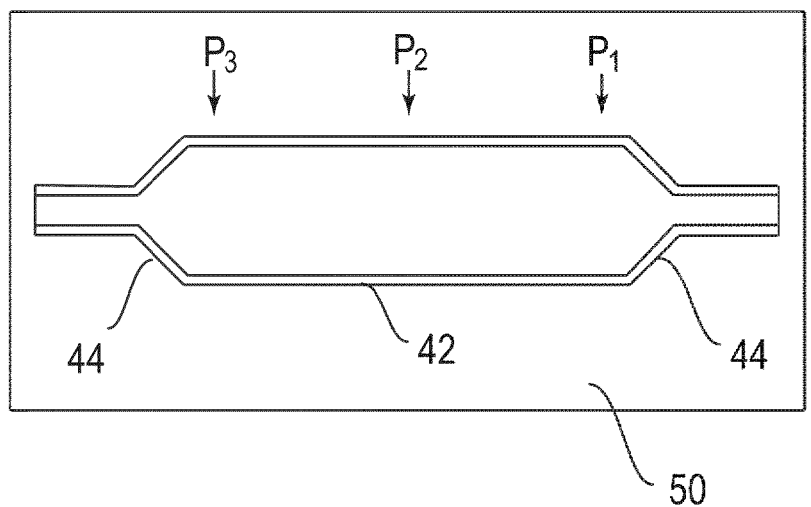
FIG. 17 is a plan view for illustrating measurement points shown in FIG. 16.

FIG. 16 is a table showing relationships between the ratio of the number of orientation distributions and the rupture in the circumferential direction in Examples 1 and 2, and Comparison Examples 1 to 5. FIG. 17 is a plan view for illustrating measurement points shown in FIG. 16.

Examples 1 and 2 are manufactured by the method of manufacturing a balloon according to the exemplary embodiment of the disclosure. Example 1 is a balloon having the three-layer structure with a length of 40 mm, and Example 2 is a balloon having the three-layer structure with a length of 30 mm. Comparison Examples 1 to 4 are balloons having the three-layer structures with lengths of 200 mm, and Comparison Example 5 is a balloon having the two-layer structure with a length of 200 mm.

Refractive index required for calculating the ratio of the number of orientation distributions is calculated by measuring retardation (a phase difference) of a test piece using a polarizing microscope. The test piece is adjusted by embedding the balloons of Examples 1 and 2 and Comparison Examples 1 to 5 in a resin 50, and performing thin slicing. A thin slice direction is the circumferential direction (a round slice direction) and the axial direction. As illustrated in FIG. 17, the measurement points in the axial direction are a distal portion side $P_1$, a center $P_2$, and a proximal portion side $P_3$ of the cylindrical portion 42.

As illustrated in FIG. 16, in Examples 1 and 2, the ratios of the numbers of orientation distributions are less than 2 throughout the total length of the cylindrical portion, and there is no occurrence of a rupture in the circumferential direction. Meanwhile, in Comparison Examples 3 to 5, the ratios of the numbers of orientation distributions are 2 or more throughout the total length of the cylindrical portion, and there is an occurrence of a rupture in the circumferential direction. In Comparison Examples 1 and 2, the ratios of the numbers of orientation distributions are partially less than 2, and there is an occurrence of a rupture in the circumferential direction. Accordingly, in order to prevent a rupture in the circumferential direction from occurring, the ratio of the number of orientation distributions needs to be less than 2 throughout the total length of the cylindrical portion.

FIGS. 18 and 19 are tables for illustrating fluctuation in the numbers of orientation distributions in Examples 3 and 4. FIG. 20 is a table for illustrating pressure resistance data of Examples 3 and 4. The numbers of orientation distributions shown in FIGS. 18 to 20 are values acquired under the condition of n=30, and fluctuation is indicated in terms of a standard deviation σ. In the ratios of the numbers of orientation distributions, only the numerical values are offset, and a result similar to that of the numbers of orientation distributions is obtained. Therefore, in FIGS. 18 and 19, calculation results of the ratios of the numbers of orientation distributions are not shown.

As illustrated in FIG. 20, with regard to the average burst pressure, the maximum burst pressure, the minimum burst pressure, and the rated burst pressure, Example 3 shows values smaller than those of Example 4. Compared to Example 4, pressure resistance is deteriorated.

Meanwhile, FIGS. 18 and 19 show that Example 3 has a greater standard deviation σ of the number of orientation distributions, compared to Example 4. In other words, the standard deviation σ of the number of orientation distributions (the ratio of the number of orientation distributions) is correlated with pressure resistance, and it is understood that as the standard deviation σ becomes lower, pressure resistance improves further.

In the balloon having a multi-layer structure, pressure resistance is significantly affected depending on the layer having the maximum strength. In Examples 3 and 4, the standard deviation σ of the outer layer having the maximum strength ranges from 0.3% to 1.0%. Accordingly, fluctuation in the axial direction in the ratio of the numbers of orientation distributions in the layer having the maximum strength is preferably 1 or less in terms of the standard deviation.

As described above, in the exemplary embodiment of the disclosure, it is possible to acquire a balloon (the balloon in which the ratio of the number of orientation distributions calculated by dividing the number of orientation distributions of the cylindrical portion in the circumferential direction by the number of orientation distributions of the cylindrical portion in the axial direction is less than 2) having a physical property in which a rupture in the circumferential direction can be prevented. In other words, it is possible to provide a balloon in which a rupture in the circumferential direction can be prevented from occurring, and to provide a method of manufacturing the same.

The disclosure herein is not limited to the above-described exemplary embodiment. For example, the medical catheter can be applied to an over-the-wire (OTW) type without being limited to a rapid exchange type. In this case, the guide wire is structured to pass through from the distal end to the user's hand. Therefore, replacement of the guide wire and operability become favorable. In addition, the load change of the chuck is not limited to the form of utilizing the load cell.

The detailed description above describes a balloon and a method of making the same. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon configured to be arranged on a medical catheter, comprising:
a dilatable cylindrical portion that is formed with a birefringent polymer material,
the dilatable cylindrical portion being configured such that a ratio of a number of orientation distributions calculated by dividing a number of orientation distributions throughout a total length of the cylindrical portion in a circumferential direction by a number of orientation distributions throughout a total length of the cylindrical portion in an axial direction is less than 2, whereby a rupture of the dilatable cylindrical portion in the circumferential direction is prevented.

2. The balloon according to claim 1,
wherein the cylindrical portion has a multi-layer structure, the birefringent polymer material including a plurality of polymer materials which are different from each other.

3. The balloon according to claim 2,
wherein fluctuation in the axial direction in the ratio of the number of orientation distributions in each layer of the multi-layer structure having a maximum strength is 1 or less in terms of a standard deviation.

4. The balloon according to claim 1,
wherein the balloon further includes a tapered portion on each end of the dilatable cylindrical portion.

5. The balloon according to claim 1,
wherein an outer diameter of the dilatable cylindrical portion is 1.0mm to 10 mm.

6. The balloon according to claim 1, wherein when a refractive index in a circumferential direction r, a refractive index in a thickness direction d, and a refractive index in an axial direction I are respectively indicated as nr, nd, and nl, $n_x$ and $n_z$ required for calculating the number of orientation distributions in the circumferential direction, the number of orientation distributions in the axial direction, and the number of orientation distributions in the thickness direction are calculated by the following Expressions 2, utilizing intrinsic refringence Δn* as a value of birefringence shown when molecules are oriented 100%:

Expressions 2

$$n_z = |\Delta n \text{ length}|/\Delta n^* \tag{5}$$

$$n_x = |\Delta n \text{ axis}|/\Delta n^* \tag{6}$$

$$|\Delta n \text{ length}| = |nl - nd| \tag{7}$$

$$|\Delta n \text{ axis}| = |nr - nd| \tag{8}$$

$$n^2 = (nr^2 + nd^2 + nl^2)/3 \tag{9}$$

wherein, $n^2$ indicates average refractive index.

7. The balloon according to claim 6, wherein
the number of orientation distributions in the circumferential direction, the number of orientation distributions in the axial direction, and a number of orientation distributions in a thickness direction are defined by the following Expressions 1:

$$\overline{\cos^2 \varnothing_x} + \overline{\cos^2 \varnothing_y} + \overline{\cos^2 \varnothing_z} = 1 \tag{1}$$

$$\overline{\cos^2 \varnothing_x} = n_z + \overline{\cos^2 \varnothing_y} \tag{2}$$

$$\overline{\cos^2 \varnothing_z} = n_x + \overline{\cos^2 \varnothing_y} \tag{3}$$

$$(1 - n_x - n_z)/3 = \overline{\cos^2 \varnothing_y} \tag{4}$$

wherein $\overline{\cos^2 \varnothing_x}$ indicates the number of orientation distributions in the circumferential direction, $\overline{\cos^2 \varnothing_y}$ indicates the number of orientation distributions in the thickness direction, and $\overline{\cos^2 \varnothing_z}$ indicates the number of orientation distributions in the axial direction.

8. A medical catheter including the balloon according to claim 1,
wherein the medical catheter is a balloon catheter.

9. The medical catheter according to claim 8,
wherein the balloon catheter is used in order to cause a stent to indwell inside a human body.

* * * * *